US011219755B2

(12) United States Patent
Siess et al.

(10) Patent No.: US 11,219,755 B2
(45) Date of Patent: Jan. 11, 2022

(54) BLOOD PUMP

(71) Applicant: ECP ENTWICKLUNGSGESELLSCHAFT MBH, Aachen (DE)

(72) Inventors: Thorsten Siess, Aachen (DE); Gerd Spanier, Aachen (DE); Jörg Schumacher, Teltow (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 208 days.

(21) Appl. No.: 15/766,698

(22) PCT Filed: Oct. 4, 2016

(86) PCT No.: PCT/EP2016/073697
§ 371 (c)(1),
(2) Date: Apr. 6, 2018

(87) PCT Pub. No.: WO2017/060254
PCT Pub. Date: Apr. 13, 2017

(65) Prior Publication Data
US 2019/0060539 A1 Feb. 28, 2019

(30) Foreign Application Priority Data
Oct. 9, 2015 (EP) .................................... 15189242

(51) Int. Cl.
*A61M 1/10* (2006.01)
*A61M 1/12* (2006.01)
(Continued)

(52) U.S. Cl.
CPC ........ *A61M 60/419* (2021.01); *A61M 60/135* (2021.01); *A61M 60/148* (2021.01);
(Continued)

(58) Field of Classification Search
CPC .. A61M 1/1036; A61M 1/1034; A61M 1/125; A61M 1/1013; A61M 1/122;
(Continued)

(56) References Cited

U.S. PATENT DOCUMENTS 4,625,712 A * 12/1986 Wampler ............ A61M 60/405
600/16
4,895,557 A 1/1990 Moise et al.
(Continued)

FOREIGN PATENT DOCUMENTS

CN 102481398 A 5/2012
CN 104225696 A 12/2014
(Continued)

OTHER PUBLICATIONS

International Search Report for PCT/EP2016/073697 dated Dec. 9, 2016 (3 pages) (English translation).
(Continued)

*Primary Examiner* — Mark W. Bockelman
(74) *Attorney, Agent, or Firm* — Botos Churchill IP Law LLP

(57) ABSTRACT

The invention relates to a blood pump. The blood pump comprises a flexible drive shaft (3) guided in a catheter, a conveying element (6) connected to the drive shaft (3) in a distal region of the drive shaft (3), and a motor (7), wherein the motor (7) has a stator (36) and a rotor (30) mounted such that it can move in the stator (36). The stator (36) comprises a winding (37) and the rotor (30) comprises a rotor magnet (31). In addition, the drive shaft (3) is connected to the rotor (30) at a proximal end of the drive shaft (3). The stator (36) and the rotor (30) are nondetachably connected to one another, and form a gap (40) with a ring-shaped cross-section, which is delimited by the rotor (30) and the stator (36).

20 Claims, 5 Drawing Sheets

Figure 1:
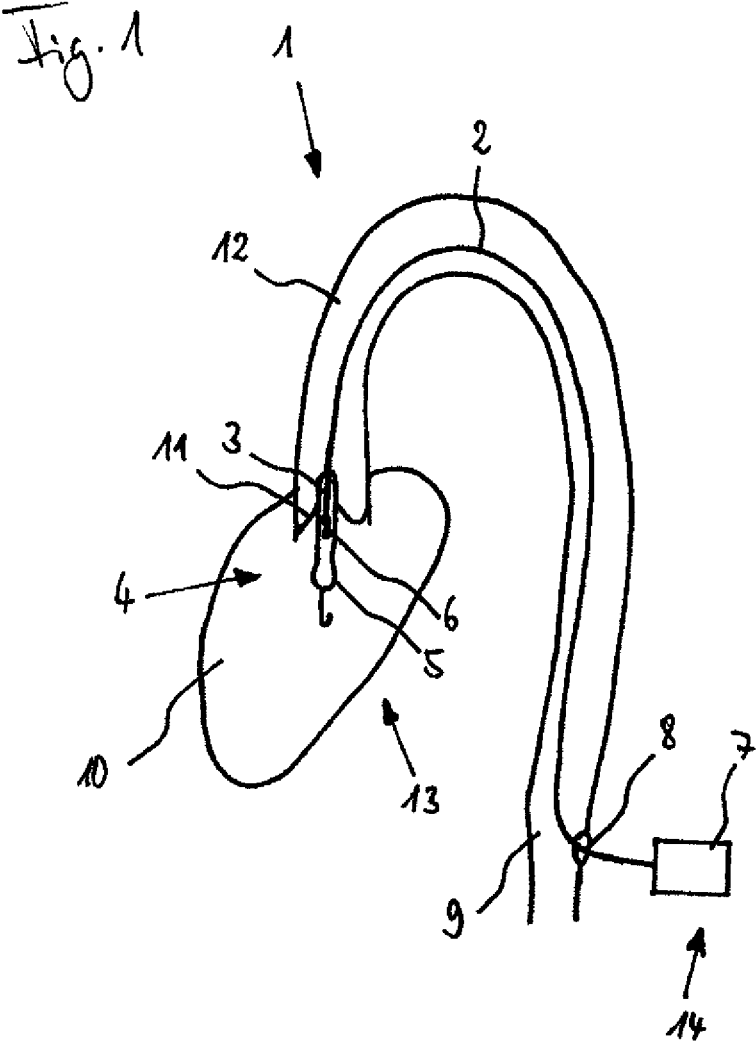

(51) Int. Cl.
*A61M 60/419* (2021.01)
*A61M 60/135* (2021.01)
*A61M 60/148* (2021.01)
*A61M 60/205* (2021.01)
*A61M 60/414* (2021.01)
*A61M 60/818* (2021.01)
*A61M 60/829* (2021.01)

(52) U.S. Cl.
CPC ........ *A61M 60/205* (2021.01); *A61M 60/414* (2021.01); *A61M 60/818* (2021.01); *A61M 60/829* (2021.01); *A61M 2205/0211* (2013.01); *A61M 2205/0238* (2013.01); *A61M 2205/3606* (2013.01)

(58) Field of Classification Search
CPC .... A61M 1/102; A61M 1/1024; A61M 1/101; A61M 2205/3606; A61M 2205/0211; A61M 2205/0238; A61M 2205/103
See application file for complete search history.

(56) References Cited

U.S. PATENT DOCUMENTS

| | | |
|---|---|---|
| 5,040,944 A | 8/1991 | Cook |
| 5,112,200 A * | 5/1992 | Isaacson ............ F04D 13/0646 415/900 |
| 6,048,363 A * | 4/2000 | Nagyszalanczy ... A61M 1/1086 623/3.13 |
| 6,387,125 B1 * | 5/2002 | Yamazaki ........... A61M 1/1074 623/3.13 |
| 2014/0010686 A1 | 1/2014 | Tanner et al. |

FOREIGN PATENT DOCUMENTS

| | | | |
|---|---|---|---|
| DE | 102007034045 | * | 1/2009 |
| GB | 802301 | * | 10/1956 |
| GB | 2505068 A | | 2/2014 |
| JP | H06181983 A | | 7/1994 |

OTHER PUBLICATIONS

Wampler et al., "In Vivo Evaluation of a Peripheral Vascular Access Axial Flow Blood Pump", Asaio Transactions, vol. 34(3): 450-454 (1988).

Office Action from corresponding Chinese Appl. No. 201680059064.6 dated Apr. 3, 2020 with English translation (12 pages).

Second Office Action from Chinese Appl. No. 2016800590646 dated Nov. 23, 2020 with English translation (12 pages).

Dadash, M.S. et al., J. Mater. Sci: Mater. Med., 22, 829-838 (2011).

Office Action from corresponding Japanese Application No. 2018-517850 dated Sep. 24, 2020 with machine generated translation (10 pages).

* cited by examiner

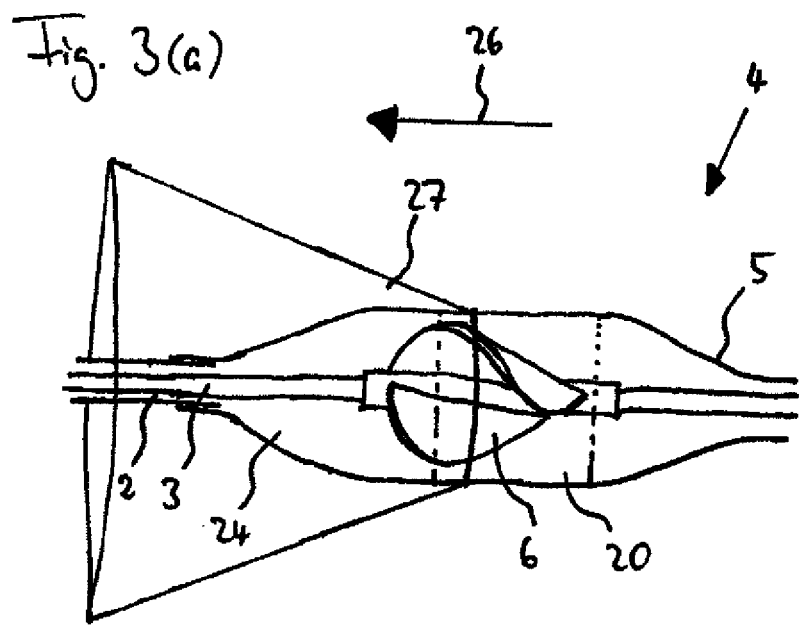
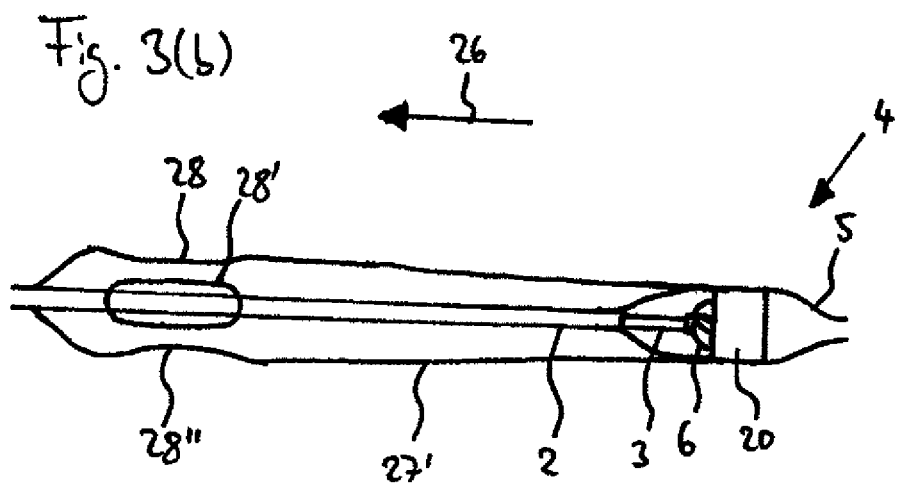

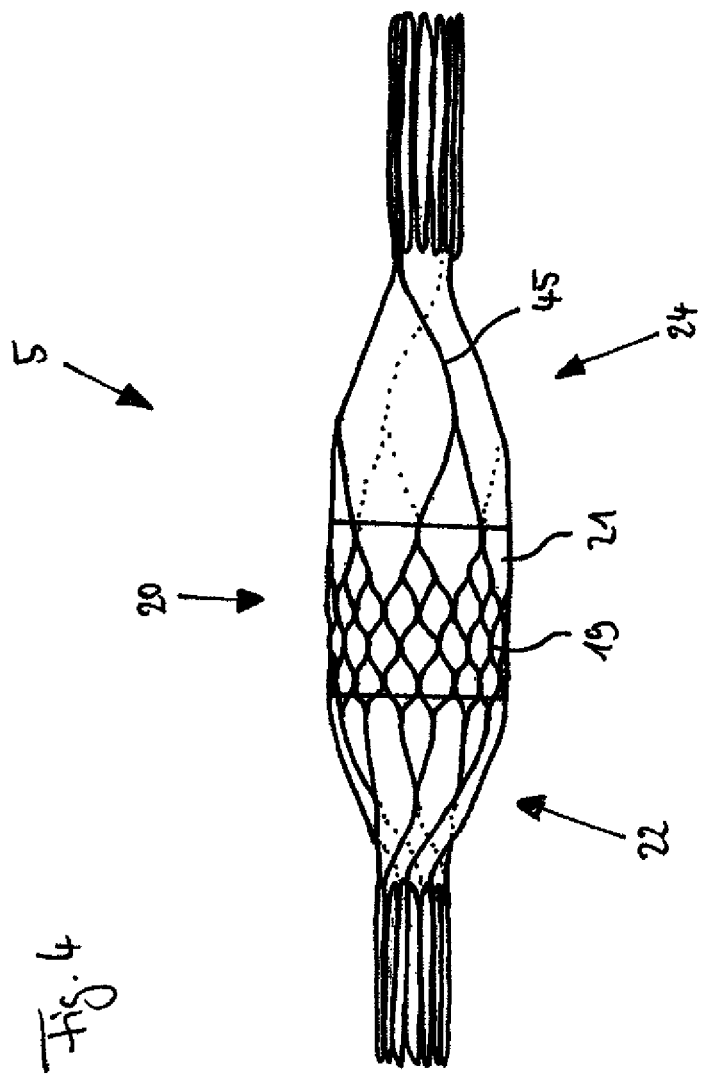

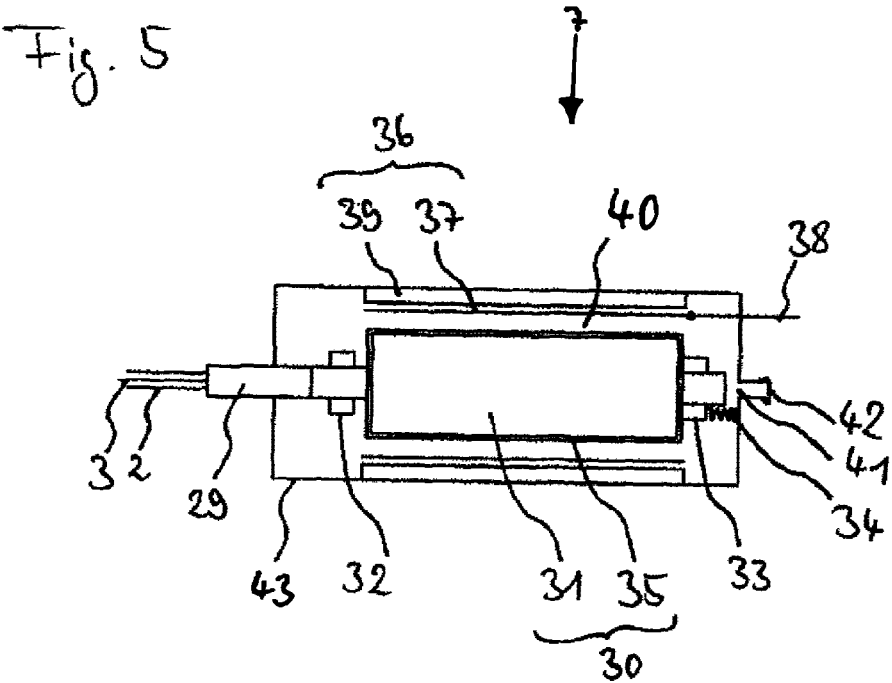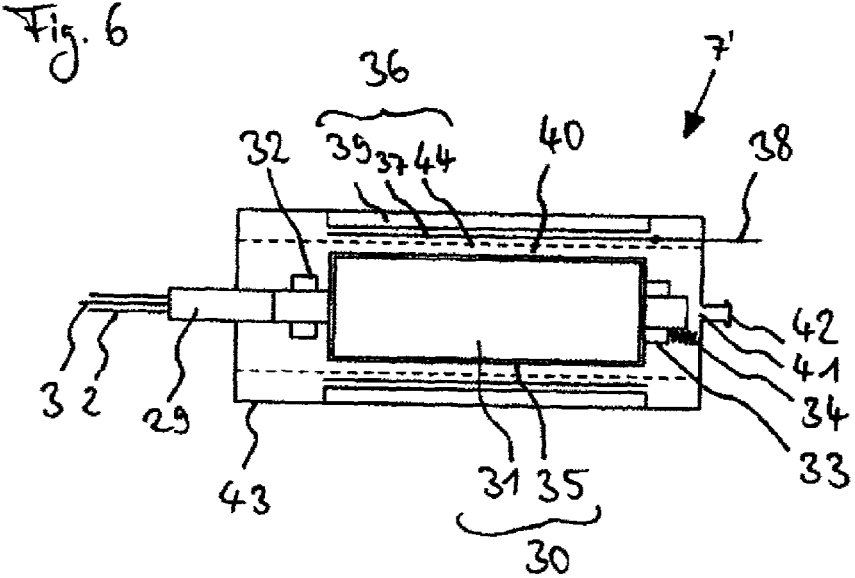

BLOOD PUMP

CROSS-REFERENCE TO RELATED APPLICATIONS

This application is a United States National Stage filing under 35 U.S. C. § 371 of International Application No. PCT/EP2016/073697, filed Oct. 4, 2016, which claims the benefit of European Patent Application No. 15189242.9, filed Oct. 9, 2015, the contents of all of which are incorporated by reference herein in their entirety. International Application No. PCT/EP2016/073697 was published under PCT Article 21(2) in English.

The application relates to a blood pump according to the preamble of claim 1. In particular, the application relates to a blood pump with a motor.

Blood pumps with a proximal and a distal end as well as with a catheter which is arranged therebetween are known from the state of the art, with regard to which pumps a flexible drive shaft is guided in an interior of the catheter. Such blood pumps at their distal end typically comprise a pump head which comprises a foldable housing and a foldable delivery element, wherein the delivery element is connected to a distal region of the drive shaft. Such pump heads can be guided to locations that are difficult to access. For example, such a pump head can be inserted through the femoral artery via the aortic arch into a region of the aortic valve of a patient, in order there to deliver blood from the left ventricle of the heart into the aorta. The drive shaft is driven at the proximal end of the blood pump by way of a motor which is typically located outside the body of the patient. Such a blood pump is described for example in the document EP 2 868 331 A2.

Document U.S. Pat. No. 4,895,557 discloses a motor arrangement for the drive of a blood pump. This motor arrangement comprises a sterilisable and fluid-tight rotor housing, in which the rotor is located. The rotor housing is designed to be guided, for operation, into a recess of the stator housing such that the rotor is surrounded by a stator. After operation, the rotor housing can be pulled out of the recess of the stator housing and disposed of.

A disadvantage of such a motor arrangement is the fact that this has quite a large volume, which can cause problems, particularly on fastening the motor arrangement to a leg of a patient. Moreover, such a motor arrangement can lead to a significant undesirable generation of heat during operation. A further disadvantage is the fact that significant contamination of the stator can occur on assembly of the system, for example due to impurities on the gloves of a user, which may necessitate an extensive cleaning and sterilisation of the reusable stator.

It is the object of the present invention to suggest a blood pump which is simple in its handling and which overcomes the disadvantages of the known devices which are mentioned above.

This object is achieved by a blood pump with the features of the main claim. Advantageous further developments result from the features of the dependent claims and of the embodiment examples.

The suggested blood pump comprises a flexible drive shaft which is guided in a catheter, a delivery element which is connected to the drive shaft in a distal region of the drive shaft, and a motor, wherein the motor comprises a stator and a rotor which is rotatably mounted in the stator. The stator comprises a winding and the rotor comprises a rotor magnet. Moreover, the drive shaft is connected to the rotor at a proximal end of the drive shaft. The stator and the rotor are non-releasably connected to one another and form a gap which is defined by the rotor and the stator.

The suggested blood pump permits a compact construction, particularly compared to the modular construction of motors for blood pumps, which are known from the state of the art and in which the rotor and the stator are designed in a manner in which they can be detached by the user. Concerning this suggested blood pump, the stator and the rotor form a unit and can be connected to one another with a for example friction bond or material bond. Through the compact construction, a reduced weight of the motor can be achieved, by which means a motor makes for a reduced load when it is fastened on the leg of a patient.

The winding can have an inner radius which corresponds maximally to 1.5 times, preferably maximally 1.25 times, particularly preferably maximally 1.15 times an outer radius of the rotor magnet. The magnetic air gap is given due to the distance between the winding and the rotor magnet. A small distance between the rotor magnet and the winding permits an efficient conversion of electrical power into pump power, so that heat losses in the motor can be kept low when operating at a desired pump power. On account of the fact that concerning the suggested motor, no housing parts need to be provided in the magnetic air gap due to the single-part construction manner, a small distance between the winding and the rotor magnet can be achieved compared to construction forms where the stator and the rotor are designed in an individually housed manner. Given an inner radius of the winding of 6 mm, the outer radius of the rotor magnet can be more than 5.25 mm, for example.

For example, a radial distance between the winding and the motor magnet can be maximally 2 mm, preferably maximally 1.25 mm, particularly preferably maximally 0.75 mm.

The gap typically has an annular cross section. The gap has a width which corresponds to a width of the magnetic air gap or which is smaller than the width of the magnetic air gap. One can envisage the gap having a width of maximally 1 mm, preferably maximally 0.5, particularly preferably maximally 0.25 mm. One can also envisage the gap having a width of at least 0.1 mm, preferably at least 0.15 mm, particularly preferably at least 0.2 mm.

A rinsing opening which is fluidically connected to the gap can moreover be provided. The rinsing opening can be fluidically connected to a rinsing connection. Such a rinsing connection can be arranged, for example, at the proximal end of the motor.

Moreover, one can envisage the gap being fluidically connected to an intermediate space which is formed between the catheter and the drive shaft. In this manner, a rinsing fluid, by way of the rinsing connection, can be rinsed through the gap into the intermediate space between the drive shaft and the catheter. By way of this, a lubrication of the drive shaft in the catheter can be achieved. Moreover, by way of introducing the rinsing fluid through the rinsing connection, one can prevent the blood of a patient from getting into the motor and in particular into the gap. A rinsing fluid can also be guided into the body of the patient through the rinsing connection, the gap and the intermediate space between the catheter and the drive shaft. For example, a glucose solution is used as a rinsing fluid.

One can envisage the rinsing fluid washing around the rotor from the proximal end to a distal end. One can also envisage the rinsing fluid washing around the rotor from its distal end to its proximal end.

Catheters with several lumens can also be used, so that a forward rinsing and return rinsing can be achieved, as is described, for example, in the document U.S. Pat. No. 4,895,557. Here, two or more connections for the rinsing fluid can be provided on the motor.

One can envisage the gap having a minimal width of 0.05 mm in order to ensure a reliable flow of rinsing fluid through the gap.

One can envisage the winding being potted into a potting compound. A potting of the winding with a potting compound is suitable for closing and levelling out possible recesses on a surface of the winding. The potting compound can comprise a low-viscous material which is suitable for flowing into the recesses and for filling these out.

One can envisage the potting compound forming a part of the stator which delimits the gap. A largely smooth boundary surface of the gap can be achieved by the potting compound. The potting compound can comprise an epoxy resin, for example. Moreover, one can also envisage the potting compound comprising, for example, aluminium oxide, iron powder or other thermally conductive substances for an improved heat transfer. By way of the potting compound, a reduced number of air bubbles adhering to the stator after a venting of the gap can be achieved.

Damage or corrosion of the winding due to a rinsing fluid or possibly due to particles transported by the rinsing fluid can be prevented by the potting compound. Moreover, by way of the potting compound, one can also prevent particles from settling on the winding.

Moreover, one can envisage the potting compound comprising a biocompatible material. Typically, the potting compound here is manufactured completely of a biocompatible material, so that no toxic substances can be released to the patient via the rising connection. For example, one can also envisage the winding being coated with parylene.

One can also envisage the stator comprising a fluid-tight sleeve with an essentially annular cross section, by way of which the gap is delimited. For example, the winding of the stator can be separated from the rising fluid by way of the sleeve. By way of this, damage to the winding due to the rinsing fluid can be prevented. One can envisage the sleeve forming a part of the stator which delimits the gap The sleeve can also be designed in a manner such that additionally to the winding, other motor parts are also separated from the rinsing fluid by the sleeve and therefore protected from damage. For example, solder locations, which may be located in the motor, can be protected from corrosion by the sleeve.

The sleeve can comprise, for example, a plastic, in particular polyether ether ketone or polyethylene, or glass. One can also envisage the sleeve being formed from an elastic plastic, which comprises, for example, polyethylene. The sleeve serves for guiding the rinsing fluid and does not necessarily serve for mechanically stabilising the motor. For this reason, it is possible to manufacture the sleeve in a thin-walled manner and/or of a flexible material. Moreover, an outer shape of the motor or of a part of the motor is not determined by the shape of the sleeve. For this reason, it can be advantageous for the sleeve to only slightly cover the winding and/or the rotor in the axial direction. For example, one can envisage the sleeve having an extension in the axial direction which is smaller than 1.5 times an axial extension of the rotor magnet.

One can also envisage the rotor being radially mounted by at least one plain bearing. For example, the rotor can be mounted by way of two plain bearings. The at least one plain bearing can comprise for example non-magnetisable materials and/or ceramic materials, in particular aluminium oxide, zirconium oxide, yttrium-stabilised zirconium oxide or silicon nitride. The plain bearing can moreover comprise, for example, steel, in particular implant steel. For example, a biocompatible coating with diamond-like amorphous carbon can also be provided.

Furthermore, the rotor can be radially mounted by way of at least one ball bearing. One can envisage the at least one ball bearing comprising non-magnetisable material. In particular, one can envisage parts of the ball bearing, at which wearing occurs due to the operation of the motor, comprising non-magnetisable material or being manufactured of a non-magnetisable material. By way of this, it is achieved that worn-away material of the parts of the ball bearing does not adhere to ferromagnetic components of the motor. By way of this, for example, ferromagnetic wear debris can be prevented from remaining stuck to the rotor and leading to a damage of the rotor. Moreover, ferromagnetic wear debris can be prevented from damaging the winding or other components of the motor.

For example, the at least one ball bearing can comprise balls having a ceramic material. Moreover, the at least one ball bearing can comprise a cage which comprises plastic. The cage for example can comprise polyethylene or polytetrafluoroethylene. The balls can also consist completely of a ceramic material. The cage can be formed completely of a plastic.

Typically, the rotor comprises a coating and/or a covering for the protection of the rotor magnet. It can be the case that the coating and/or the covering forms a part of the rotor which part delimits the gap. The coating as well as the covering can comprise biocompatible material or consist of a biocompatible material. For example, a coating with parylene or a biocompatible epoxy resin can be provided. A coating of diamond-like amorphous carbon can also be provided. The coating can have a thickness which is less than 100 µm, preferably less than 10 µm. The rotor for example can comprise a covering of polyether ether ketone or stainless steel.

The blood pump can comprise an unfoldable pump head which comprises the delivery element and a housing, wherein the delivery elements and the housing are designed in a manner such that these automatically unfold after a forced compression. An unfoldable pump head permits a relatively large design of the pump head and of the delivery elements while permitting a relatively small diameter of an opening for inserting the blood pump in the tissue of a patient.

Typically, the pump is configured to pump blood from a ventricle into a blood vessel of a patient when the motor is arranged outside the body of the patient. The motor can be configured for example for being fastened to a thigh of the patient.

For this, the flexible drive shaft has an adequate length which is dependent on the anatomy of the patient. Typically, the flexible shaft here has a length of at least 50 cm, preferably at least 90 cm. A maximal length of the flexible drive shaft is 200 cm, preferably 150 cm With the use of a blood pump which is driven by a motor located outside a patient, higher demands on the efficiency may need to be fulfilled compared with blood pumps which are driven by a motor in the body of a patient. The removal of the heat produced on operation via the blood system of the patient is advantageous for example for a motor which is arranged in the inside of the patient's body. In contrast, a pump which produces heat and is arranged outside the body of the patient under certain circumstances requires further elements for the dissipation of heat or a particularly efficient operating manner The application moreover relates to an operating method for the suggested blood pump. When this operating method is used, a touchable surface of a housing of the motor heats to a temperature of not more that 60° C., preferably of not more than 48° C., particularly preferably not more than 43° C., during a permanent operation at a speed of 15,000, preferably at least 30,000 r.p.m. Particularly on fastening the motor to a thigh of a patient, it is important for the housing of the motor not to heat up too much on operation.

Moreover, an operating method is envisaged in which touchable surfaces of the housing of the motor do not heat to a temperature of more than 60° C., preferably not more than 48° C., particularly preferably not more than 43° C. during a permanent operation of the blood pump at a delivery rate of at least 1 l/min, preferably at least 2 l/min.

One can envisage the blood pump comprising a cooling body, for example with cooling ribs which are connected to the motor in a thermally conductive manner, or a heat tube, for dissipating heat which is created on operation. One can also envisage the blood pump being configured for dissipating heat onto the tissue of a patient, for example via the skin of the thigh.

The blood pump with all described components can be delivered in a sterile packaged manner. The blood pump can be sterilised for example by way of gamma sterilisation or by using ethylene oxide. The blood pump can be completely disposed of after its use. A repeated cleaning or sterilisation of parts of the blood pump, in particular of the motor, by the user can thus be dispensed with in the case of the suggested blood pump.

Figure 2:
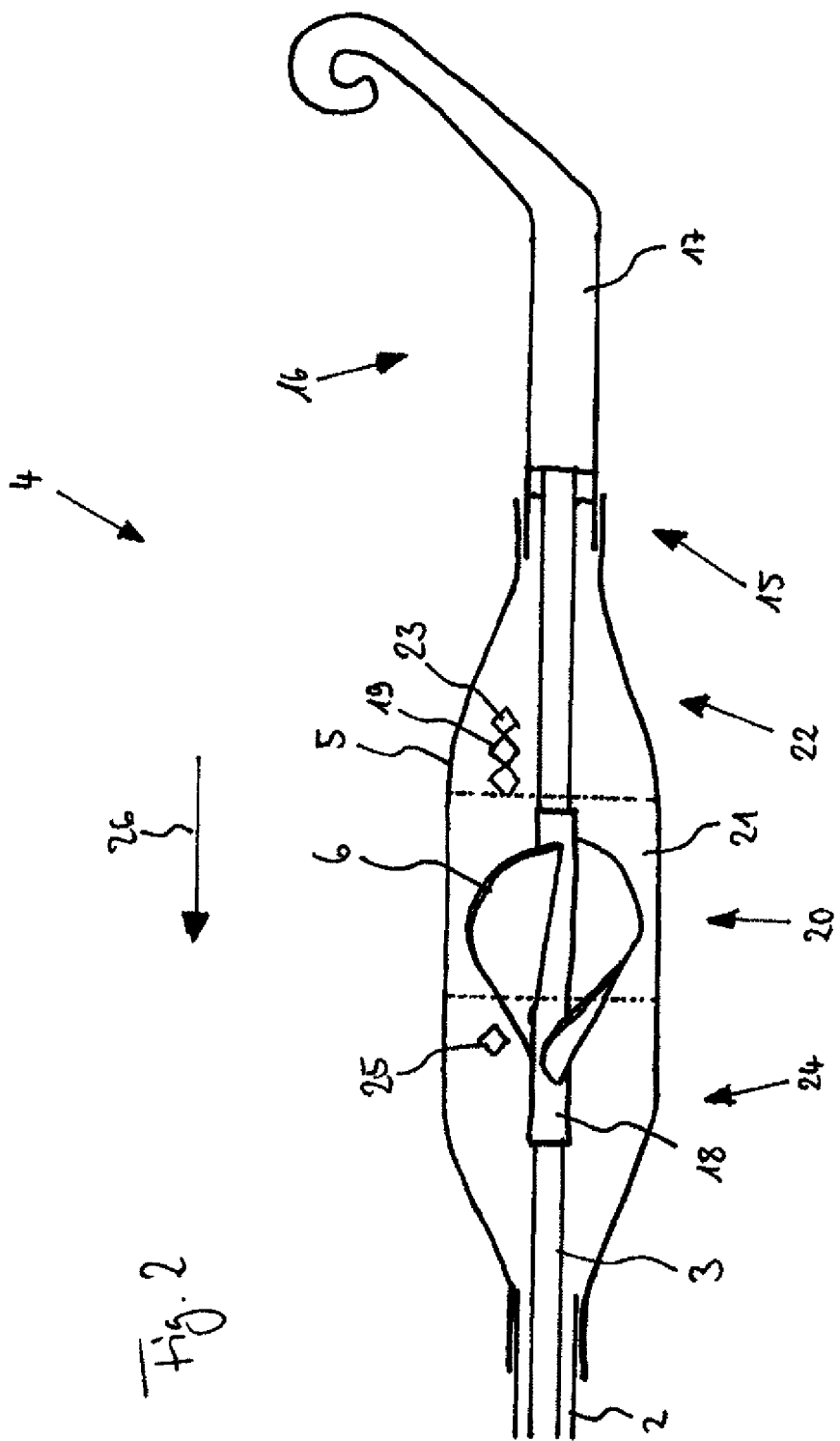

Embodiment examples of the invention are hereinafter described by way of the diagrams. There are shown in:

FIG. 1 a schematic representation of a pump arrangement,

FIG. 2 a schematic representation of a pump head,

FIGS. 3(a), (b) two further schematic representations of the pump head,

FIG. 4 a schematic representation of a housing,

FIG. 5 a schematic representation of a motor and

FIG. 6 a schematic representation of a further motor.

FIG. 1 schematically shows a pump arrangement 1. The pump arrangement 1 comprises a catheter 2, in which a flexible drive shaft 3 is guided. The catheter 2 is connected to a pump head 4. This pump head 4 comprises a housing 5 and a delivery element 6 which is arranged in the housing 5 and which can be driven via the drive shaft 3 by a motor 7 connected to the proximal end of the drive shaft 3. The pump head 4 as well as the catheter 2 and the drive shaft 3 are introduced into the femoral artery 9 via a port 8, in a manner such that the pump head 4 in the region of the left ventricle 10 is located in the region of the aortic valve 11. On operation, the drive shaft 3 is driven by the motor 7 and the pump arrangement 1 delivers blood from the left ventricle 10 into the aorta 12. In the shown arrangement for left heart assistance, a delivery direction of the pump arrangement 1 corresponds to the direction from a distal end 13 of the pump arrangement 1 to a proximal end 14 of the pump arrangement 1.

However, the pump arrangement 1 can also be configured for a delivery of blood in a direction from the proximal end 14 to the distal end 13 of the pump arrangement 1, which is suitable for example for right heart assistance.

The pump head 4 is represented schematically in FIG. 2. Recurring features in this and in the subsequent drawings are provided with the same reference numerals. The pump head 4 comprises the delivery element 6 and the housing 5. The delivery element 6 in the present example is designed as a pump rotor with two flexible segments in the form of rotor blades. Additionally, the drive shaft 3, which is mounted on a distal region 15 of the pump head 4, is represented. A so-called pigtail 17, which is manufactured from an elastically deformable material, is provided at the distal end 16 of the pump head 4. A cylindrical element 18 is rigidly connected to the drive shaft 3. The delivery element 6 is fastened onto the cylindrical element 18. The delivery element 6 as well as the housing 5 are designed in such an unfoldable manner that they can automatically unfold after a forced compression. The delivery element 6 is manufactured from a plastic. The housing 5 is manufactured from the shape memory material nitinol. The complete pump head 4 can be unfolded due to the fact that the delivery element 6 as well as the housing 5 are designed in an unfoldable manner.

The housing 5 is designed as a rhomboidal lattice 19 and in a fluid-tight region 20 comprises an elastic covering 21 of polyurethane. The elastic covering 21 covers an inner side and an outer side of the rhomboidal lattice 19 in a manner such that rhomboid lattice openings which are formed by the lattice 19 in the fluid-tight region 20 can be closed in a fluid-tight manner by way of the elastic covering 21.

The housing 5 moreover comprises an inlet region 22 which is not covered by the elastic covering 21. In the inlet region 22, the rhomboid lattice openings form inlet openings, of which one is provided, by way of example, with the reference numeral 23 in FIG. 2. The housing 5 moreover comprises an outlet region 24 which is likewise not covered by the elastic covering 21. In the outlet region 24, the rhomboid-like lattice openings form outlet openings, of which one is represented by way of example and is provided with the reference numeral 25.

On operation of the pump arrangement 1, the drive shaft 3 is driven by the motor 7, so that the delivery element 6, which is connected to the drive shaft 3, rotates about an axis of the drive shaft 3. By way of this, blood is transported through the inlet openings of the inlet region 22 into the housing 5 and subsequently exits through the outlet openings of the outlet region 24, out of the housing 5. Blood is delivered in a delivery direction 26 by way of the pump arrangement 1 in this manner.

The elastic covering 21 does not completely surround the axial extension of the delivery element 6. Instead, the delivery element 6 projects partly into the outlet region 24, so that at least the outlet opening with the reference numeral 25 is arranged laterally, i.e. in the radial direction, next to the delivery element 6. In contrast, the elastic covering 21 at its distal end is designed in a manner such that the delivery element 6 does not project or does not significantly project into the inlet region 22 and is therefore not laterally surrounded by the inlet openings.

The design of the elastic membrane 21 and the delivery element 6 and their arrangement with respect to one another is such that roughly a third of the axial extension of the delivery element 6 is not surrounded by the elastic membrane 21 which forms the fluid-tight region 20. In the shown example, the same share of the axial extension of the delivery element 6 is surrounded by the outlet region 24.

The pump head 4 additionally comprises an outflow element. This can be designed as an outflow shield 27 as is represented in FIG. 3(a), or as an outflow tube 27' as is represented in FIG. 3(b).

The outflow shield 27, which is represented in FIG. 3(a), is fastened to the housing 5 in the fluid-tight region 20 of the housing 5. The outflow shield 27 has the shape of a lateral surface of a truncated cone and extends in the delivery direction 26 such that this shield is widened in the delivery direction 26. The delivery element 6 and the outlet region 24 are surrounded by the outflow shield 27. In another embodiment, one can also envisage the outlet region 24 being partly surrounded by the outflow shield 27

The pump head 4 in FIG. 3(*b*) only differs from the pump head 4 represented in FIG. 3(*a*) in that an outflow tube 27' is provided instead of the outflow shield 27. This outflow tube 27' is fastened to the housing 5 in the fluid-tight region 20 and extends from there in the delivery direction 26. The outflow tube 27' is manufactured from polyurethane and comprises openings 28, 28', 28" in a region situated in the delivery direction 26. In the example shown, the outlet region 24 is completely surrounded by the outflow tube 27'. The outflow tube 27' is flexible and closes automatically when a blood flow occurs in a direction that is opposite to the delivery direction 26, due to the outflow tube 27' being pressed onto the catheter 2 and/or onto the housing 5.

FIG. 4 schematically shows the rhomboidal lattice 19 of the housing 5. The fluid-tight region 20 with the elastic covering 21 as well as the inlet region 22 and the outlet region 24 are additionally represented. Regions of the inlet region 22 and of the outlet region 24 have a conical shape, whereas the fluid-tight region 20 is essentially tubular. The lattice 19 comprises lattice struts, of which one is characterised by way of example by the reference numeral 45. The lattice struts 45 run in a manner such that the essentially rhomboidal lattice openings are larger in the inlet region 22 as well as in the outlet region 24 than in the fluid-tight region 20. Lattice struts which are arranged on a side of the housing 5 which is away from the viewer are merely represented in FIG. 4 in a dotted manner for an improved overview.

In the fluid-tight region 20, the lattice struts 45 form a comparatively finely meshed lattice. The lattice 19, along a peripheral of the housing 5 in the fluid-tight region 20, comprises thirty-two struts or, inasmuch as the periphery is considered at an axial position of the housing 5 with node points, comprises sixteen nodes. A largely round cross section of the housing 5 in the fluid-tight region 20 is achieved by way of such a close-meshed lattice 19.

The number of lattice struts 45 along a periphery of the housing 5 is halved from the fluid-tight region 20 in the direction of the inlet region 22 and in the direction of the outlet region 24 by way of merging the lattice struts into pairs, so that the housing 5 in the corresponding regions comprises sixteen lattice struts 45 along the periphery, in which no node points are present. The number of lattice struts 45 is subsequently reduced once again in the direction of the inlet region 22 and of the outlet region 24, by way of merging the lattice struts into pairs, so that the housing 5 in these regions comprises eight lattice struts 45. A further reduction of the number of lattice struts 15 is effected in the outlet region 24 in the manner mentioned above, so that the housing 5 in a region situated further in the delivery direction 26 has only four lattice struts 45 along a periphery.

A lattice 19 with larger lattice openings than in the fluid-tight region 20 forms in the inlet region 22 and in the outlet region 22 on account of the described reduction of the number of lattice struts 45.

The lattice struts 45 in the conical regions of the outlet region 24 and of the inlet region 22 form a spiral-shaped structure, which leads to a reliable unfolding of the pump head 4 when pushing the pump head 4 out of a cannula.

FIG. 5 shows a schematic view of the motor 7. The motor 7, in the region of a shaft stub 29, is connected to the catheter 2, which is glued into the shaft stub 29. The flexible drive shaft 3 is guided in the catheter 2. The motor 7 moreover comprises a rotor 30, which has a rotor magnet 31.

The flexible drive shaft 3 is connected to the rotor 30 in a manner such that given a rotation of the rotor 30, a torque is transmitted from the rotor 30 to the flexible drive shaft 3. The torque is transmitted to the delivery element 6 via the flexible drive shaft, so that the pump arrangement is driven by the motor 7.

The rotor 30 is axially mounted by way of two bearings 32, 33. One of these bearings 33 is biased by way of a spring element 34 for an axial stabilisation of the rotor 30. The spring element 34 can be designed, for example, as a helical spring or as an annular spring. The bearings 32, 33 can each be designed as ball bearings or as plain bearings. If the bearings 32, 33 are designed as ball bearings, then the bearings 32, 33 comprise balls of ceramic and cages of plastic so that the ball bearings have non-magnetisable material. The rings of the bearings can be designed for example from a magnetisable metal or from a non-magnetisable material. If the bearings 32, 33 are designed as plain bearings, then they each comprise friction partners of DLC-coated implant steel and yttrium-stabilised zirconium oxide.

The rotor magnet 31 comprises a biocompatible DLC coating. The motor 7 moreover comprises a stator 36. The stator 36 comprises several windings 37 which are connected in an electrically conductive manner to electricity connections 38. The stator 36 moreover comprises back iron laminations 39. The windings 37 are potted with a biocompatible epoxy resin which contains thermally conductive aluminium oxide.

A gap 40 with an annular cross section is formed between an inner side of the coating of the windings 37 and an outer side of the coating 35 of the rotor magnet 31. The gap 40 has a width of 0.2 mm. This gap 40 is in fluid connection with a rinsing opening 41, which is connected to a rinsing connection 42, wherein the rinsing connection 42 is arranged at a proximal end of the motor 7. The gap 40 is moreover in fluid connection with an intermediate space formed between the drive shaft 3 and the catheter 2. Thus, for example, a glucose solution can be rinsed through the rinsing opening 41 and the gap 40 and the intermediate space via the rinsing connection 42. Glucose solution rinses around the rotor 30 during operation in this manner. A radial distance between the outer side of the rotor magnet 31 and an inner side of the windings 37 is 0.5 mm. An inner radius of the windings 37 here corresponds to 1.1 times an outer radius of the rotor magnet 31.

The stator 36 and the rotor 30 are connected to one another in a manner that cannot be released by the user and are incorporated into a motor housing 43. The motor housing 43 can be connected, for example, to a grip or to a cooling body. The motor can be operated in a very efficient manner due to the small distance between the windings 37 and the rotor magnet 31, so that the motor housing 43 as well as a grip or cooling body, which may be connected to this housing, is heated to less than 40° C. at its exposed surfaces when the pump arrangement 1 is operated at a speed of 32,000 r.p.m and at a delivery output of 2.5 l per minute.

The motor 7' which is represented in FIG. 6 differs from the motor 7 represented in FIG. 5 merely in that the stator 36 in this embodiment comprises a fluid-tight sleeve 44 which delimits the gap 40. In this embodiment, the width of the gap 40 for example is 0.15 mm or 0.22 mm. The sleeve 44 comprises polyether ether ketone and is magnetically inactive. The sleeve 44 is arranged in a manner such that for example the windings 37 and further parts of the stator 36 are separated from the rinsing fluid which possibly flows through the gap 40, by way of the sleeve 44. An extension of the sleeve 44 in the axial direction is about 1.2 times an axial extension of the rotor magnet 31.

Features of the different embodiments which are merely disclosed in the embodiment examples can be combined with one another and claimed individually.

The invention claimed is:

1. A blood pump, comprising:
   a pump housing having a blood flow inlet and a blood flow outlet;
   a flexible drive shaft which is positioned in a lumen of a catheter, wherein the lumen of the catheter is in fluid communication with the pump housing;
   a delivery element which is connected to the flexible drive shaft in a distal region of the flexible drive shaft; and
   a motor having a motor housing configured to be arranged outside a body of a patient, wherein the motor comprises:
      a stator and
      a rotor which is rotatably mounted in the stator,
   wherein the flexible drive shaft is connected to the rotor at a proximal end of the flexible drive shaft, and wherein the stator and the rotor are connected to one another and form a gap which is delimited by the rotor and the stator,
   wherein the motor housing comprises a rinsing opening which is fluidically connected to the gap,
   wherein, during operation of the blood pump, blood enters the pump housing through the blood flow inlet, the motor drives the flexible drive shaft, the flexible drive shaft rotates the delivery element, and the blood exits the pump housing through the blood flow outlet, and,
   wherein the rinsing opening, the gap, and the lumen of the catheter are in fluid communication such that, during operation of the blood pump, a rinsing fluid introduced into the rinsing opening passes through the gap and the lumen of the catheter and exits the lumen of the catheter into the pump housing.

2. The blood pump according to claim 1, wherein the gap has a width of at most 1 mm.

3. The blood pump according to claim 1, wherein the gap is fluidically connected to an intermediate space which is formed between the catheter and the flexible drive shaft.

4. The blood pump according to claim 1, wherein the gap has a minimal width of 0.05 mm.

5. The blood pump according to claim 1, wherein the stator comprises a winding and the rotor comprises a rotor magnet, and the winding has an inner radius which is at most 1.5 times an outer radius of the rotor magnet.

6. The blood pump according to claim 5, wherein a radial distance between the winding and the rotor magnet is at most 2 mm.

7. The blood pump according to claim 5, wherein the winding is potted into a biocompatible potting compound.

8. The blood pump according to claim 5, wherein the rotor has a coating or a cover for protection of the rotor magnet.

9. The blood pump according to claim 8, wherein the gap is formed between an outer side of the coating or the cover of the rotor and an inner side of the winding of the stator.

10. The blood pump according to claim 1, wherein the stator comprises a fluid-tight sleeve with an essentially annular cross section, by way of which the gap is delimited.

11. The blood pump according to claim 10, wherein the rotor comprises a rotor magnet and wherein the fluid-tight sleeve has an extension in an axial direction which is smaller than 1.5 times an axial extension of the rotor magnet.

12. The blood pump according to claim 1, wherein the rotor is radially mounted by at least one plain bearing.

13. The blood pump according to claim 1, wherein the rotor is radially mounted by at least one ball bearing.

14. The blood pump according to claim 13, wherein the at least one ball bearing comprises non-magnetisable material.

15. The blood pump according to claim 14, wherein the at least one ball bearing comprises balls which comprise a ceramic material.

16. The blood pump according to claim 13, wherein the at least one ball bearing comprises a cage which comprises a plastic.

17. The blood pump according to claim 1, wherein the flexible drive shaft has a length sufficient to connect the delivery element arranged inside a ventricle with the motor arranged outside the body of the patient.

18. The blood pump according to claim 1, comprising an unfoldable pump head which encompasses the delivery element and the pump housing, wherein the delivery element and the pump housing are designed to automatically unfold after a forced compression.

19. The blood pump according to claim 1 wherein the gap has a width of at least 0.1 mm.

20. The blood pump according to claim 1, wherein touchable surfaces of a housing of the motor are configured to heat up to a temperature of not more than 60 degrees C. while the rotor is configured to spin at a speed of 15,000 r.p.m.

* * * * *

UNITED STATES PATENT AND TRADEMARK OFFICE
CERTIFICATE OF CORRECTION

| | |
|---|---|
| PATENT NO. | : 11,219,755 B2 |
| APPLICATION NO. | : 15/766698 |
| DATED | : January 11, 2022 |
| INVENTOR(S) | : Thorsten Siess et al. |

It is certified that error appears in the above-identified patent and that said Letters Patent is hereby corrected as shown below:

In the Specification

Column 3, Line 40:
Now reads: "gap"; should read -- gap. --

Column 4, Line 56:
Now reads: "150 cm"; should read -- 150 cm. --

Column 4, Line 67:
Now reads: "manner"; should read -- manner. --

Column 5, Line 4:
Now reads: "that"; should read -- than --

Column 5, Line 15:
Now reads: "1 l/min,"; should read -- 1 l/min, --

Column 5, Line 15:
Now reads: "2 l/min."; should read -- 2 l/min. --

Column 7, Line 4:
Now reads: "27"; should read -- 27. --

Column 7, Line 8:
Now reads: "27"; should read -- 27' --

Column 7, Line 51:
Now reads: "15"; should read -- 45 --

Signed and Sealed this
Ninth Day of August, 2022

Katherine Kelly Vidal
*Director of the United States Patent and Trademark Office*

CERTIFICATE OF CORRECTION (continued)
U.S. Pat. No. 11,219,755 B2

Column 7, Line 57:
Now reads: "22"; should read -- 24 --

In the Claims

Column 9, Claim 1, Line 18:
Now reads: "stator"; should read -- stator, --

Column 9, Claim 1, Line 31:
Now reads: "and,"; should read -- and --